United States Patent [19]

Küng

[11] Patent Number: 5,407,934
[45] Date of Patent: Apr. 18, 1995

[54] FUNGICIDAL COMPOSITIONS

[75] Inventor: Ruth Küng, Dielsdorf, Switzerland

[73] Assignee: Ciba-Geigy Corporation, Ardsley, N.Y.

[21] Appl. No.: 231,954

[22] Filed: Apr. 21, 1994

Related U.S. Application Data

[63] Continuation of Ser. No. 5,202, Jan. 15, 1993, abandoned, which is a continuation of Ser. No. 893,962, Jun. 4, 1992, abandoned, which is a continuation of Ser. No. 784,201, Oct. 28, 1991, abandoned.

[30] Foreign Application Priority Data

Nov. 2, 1990 [CH] Switzerland ............... 3489/90

[51] Int. Cl.⁶ ............... A01N 43/64; A01K 31/535
[52] U.S. Cl. ................... 514/239.5; 514/383
[58] Field of Search ............... 514/239.5, 383

[56] References Cited

U.S. PATENT DOCUMENTS

| | | | |
|---|---|---|---|
| 4,241,058 | 12/1980 | Pfiffner | 424/248.4 |
| 4,664,696 | 5/1987 | Schaub | 71/92 |
| 4,835,169 | 5/1990 | Wiedmer | 514/383 |
| 4,925,842 | 5/1990 | Janicke | 514/239 |

OTHER PUBLICATIONS

Royal Society of Chemistry (1987), Second Edition 5 pages,.
Bush et al., C.A., vol. 110 (1989) 110:207691m.
Worthing et al., The Pesticide Manual, 8th Ed. (1987) p. 383.

*Primary Examiner*—Allen J. Robinson
*Attorney, Agent, or Firm*—Edward McC. Roberts

[57] ABSTRACT

Plant fungicidal compositions based on two active ingredients a) and b) show a synergistically increased effect in the case where component a) is 2-(4-chlorophenyl)-3-cyclopropyl-1-[(1H-1,2,4-triazol-1-yl)butan-2-ol and component b) is either fenpropimorph or fenpropidin or a mixture of the two.

5 Claims, No Drawings

FUNGICIDAL COMPOSITIONS

This application is a continuation of application Ser. No. 08/005,202 filed Jan. 15, 1993, now abandoned, which is a continuation of Ser. No. 07/893,962 filed Jun. 4, 1992, now abandoned, which is a continuation of Ser. No. 07/784,201 filed Oct. 28, 1991, now abandoned.

FUNGICIDAL COMPOSITIONS

The present invention relates to novel active substance combinations for controlling plant diseases and to processes for applying such mixtures for leaf, soil and seed dressing application.

The combinations according to the invention comprise a) 2-(4-chlorophenyl)-3-cyclopropyl-1-[(1H-J-1,2,4-triazol-1-yl)butan-2-ol of the formula I

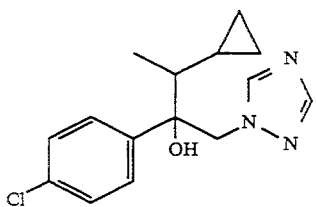

or acid addition salts and metal complexes thereof, and b) cis-4-[3-(4-tert-butylphenyl)-2-methylpropyl]-2,6-dimethylmorpholine of the formula II

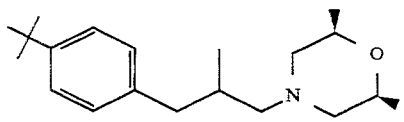

or acid addition salts thereof and/or 1-[3-(4-tert-butylphenyl)-2-methylpropyl]piperidine of the formula III

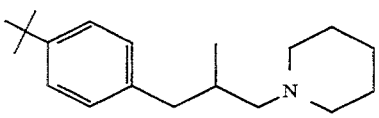

or acid addition salts thereof.

Component a) has become known under the name cyproconazol. Its synthesis and fungicidal properties are described in German Offenlegungsschrift 34 06 993.

Component b) has become known under the name fenpropimorph and component c) under the name fenpropidin. Their syntheses and fungicidal properties are described in German Offenlegungsschrift 2 752 135.

Surprisingly, it was found that the fungicidal action of the active ingredient (a.i.) combination according to the invention is significantly higher than the sum of the actions of the individual active substances. This means that an unforeseeable synergistically increased action is present and not only an additive action as could have been expected by the combination of two active substances. The active substance combinations according to the invention thus constitute an enlargement of the art.

When the active substances are present in the active substance combinations (hereafter called the mixtures) according to the invention in specified weight ratios, the synergistic effect is particularly apparent. However, the weight ratios of the active substances in the active substance combinations can be varied within a relatively wide range, depending on the type of application. In general, 0.2–20 parts by weight, preferably 0.5–10 parts by weight of active substance(s) of the formula (II) and/or (III) are present per part by weight of active substance of the formula (I). This corresponds to a weight ratio of component a) to component b) of 5:1 to 1:20. Particular preference is given to combinations in which 1 to 8 parts by weight of active substance(s) of the formula (II) and/or (III) are present per part by weight of the formula (I), in particular a):b)=2:1 to 1:10 and very particularly 1:1 to 1:4. Examples of mixing ratios of a):b) which are particularly suitable for practical application are 2:3; 2:5; 1:2 and 1:3. The above weight ratios apply regardless of whether the active components' acid addition salts or metal complexes are used.

Examples of acids which can be used for preparing salts of the formula I, II or III are: hydrohalic acids such as hydrobromic acid and hydrochloric acid, furthermore phosphoric acid, nitric acid and sulfuric acid, furthermore mono-, bi- or trifunctional carboxylic acids and hydroxycarboxylic acids such as formic acid, succinic acid, acetic acid, glycolic acid, fumaric acid, lactic acid, oxalic acid, propionic acid, sorbic acid, trichloroacetic acid, trifluoroacetic acid, citric acid, furthermore sulfonic acids such as benzenesulfonic acid, 1,5-naphthalenedisulfonic acid and p-toluenesulfonic acid and (thio)saccharin.

Metal complexes consist of the basic organic molecule and an inorganic or organic metal salt, for example halides, nitrates, sulfates, phosphates, acetates, trifluoroacetates, trichloroacetates, propionates, tartrates, sulfonates, salicylates, benzoates, and the like, of the elements of main group III or IV, such as aluminium, tin or lead and of subgroup I to VIII, such as chromium, manganese, iron, cobalt, nickel, copper, zinc, and the like. Preference is given to subgroup elements from the 4th period. In these metal complexes, the metals can be present in the various valencies in which they usually occur.

The active substance mixtures according to the invention and acid addition salts thereof have plant fungicidal action and can therefore be used for controlling fungi in agriculture and horticulture. They are suitable in particular for inhibiting the growth of or for destroying phytopathogenic fungi on parts of plants, for example leaves, stalks, roots, tubers, fruits or flowers, and on seeds and of harmful fungi present in the soil.

The active substance mixtures according to the invention are suitable in particular for controlling ascomycetes (*Erysiphe graminis, Uncinula necator*, Venturia, *Sphaerotheca pannosa, Erysiphe betae*) and basidiomycetes, which include rusts, for example those of the genera Puccinia, Uromyces and Hemileia (in particular *Puccinia recondita, Puccinia striiformis, Puccinia graminis, Puccinia coronata, Uromyces fabae, Uromyces appendiculatus, Hemileia vastatrix*). Furthermore, the active substance combinations according to the invention act against *Fungi imperfecti* of the genera Helminthosporium (for example *Helminthosporium oryzae, Hehninthosporium teres, Helminthosporium sativum, Helminthosporium tritici-repentis*), Alternaria (for example *Al-*

*ternaria brassicola, Alternaria brassicae*), Septoria (for example *Septoria avenae*), Cercospora (for example *Cercospora beticola*), Ceratocystis (for example *Ceratocystis ulmi*), Pyricularia (for example *Pyricularia oryzae* and *Mycospharella fijiensis*).

The active substance combinations according to the invention are suitable in particular also for controlling mould strains which have developed a certain resistance towards active substances from the class of triazoles.

In the field, it is preferred to use dosages of 75 to 1000 g of active substance mixture per hectare and treatment. For controlling fungi in dressing treatments of seeds, dosages of 0.01 g to 1.0 g of active substance mixture are advantageously used per kg of seed. Analogously, these data also apply to plant propagation material, i.e. in general also for kg amounts of cuttings, tubers, root material, and the like.

The fungicide combinations according to the invention are distinguished by systemic, curative and preventive action.

The active substance mixtures according to the invention can be formulated to give a wide range of agents, for example solutions, suspensions, emulsions, emulsifiable concentrates and pulverulent preparations. The present invention also relates to the fungicidal compositions of this type. The fungicidal compositions according to the invention comprise an effective amount of cyproconazol and fenpropimorph and/or fenpropidin or acid addition salts or metal complexes of these active substances and formulation agents. Advantageously, the compositions contain at least one of the following formulation agents: solid carriers; solvents or dispersants; surfactants (wetting agents and emulsifiers); dispersants (without surfactant action); and additives of other types, such as stabilisers.

Suitable solid carriers are in particular: natural minerals, such as kaolin, clays, kieselguhr, talc, bentonite, chalk, for example whiting, magnesium carbonate, limestone, quartz, dolomite, attapulgite, montmorillonite and diatomaceous earth; synthetic minerals, such as highly disperse silica, alumina and silicates; organic materials, such as cellulose, starch, urea and synthetic resin; and fertilisers, such as phosphates and nitrates, it being possible for carriers of this type to be present, for example, as granules or powders.

Suitable solvents or dispersants are mainly: aromatics, such as toluene, xylenes, polyalkylated benzenes and alkylnaphthalenes; chlorinated aromatics and chlorinated aliphatic hydrocarbons, such as chlorobenzenes, chloroethylenes and methylene chloride; (cyclo)aliphatic hydrocarbons, such as cyclohexane and paraffins, for example petroleum fractions; alcohols, such as butanol and glycol, and ethers and esters thereof; ketones, such as acetone, methyl ethyl ketone, methyl isobutyl ketone, isophorone and cyclohexanone; and strongly polar solvents and dispersants, such as dimethylformamide, N-methylpyrrolidone and dimethyl sulfoxide, solvents and dispersants of this type preferably having flash points of at least 30° C. and boiling points of at least 50° C., and water. Of the solvents and dispersants, so-called liquefied gaseous extenders or carriers are also suitable. These are products which are gaseous at room temperature and under atmospheric pressure. In the case where water is used as the solvent, it is possible, for example, also to use organic solvents as solvent aids.

The surfactants (wetting agents and emulsifiers) can be nonionic compounds, such as condensation products of fatty acids, fatty alcohols or fat-substituted phenols with ethylene oxide; fatty acid esters and ethers of sugars or polyhydric alcohols; products obtained from sugars or polyhydric alcohols by condensation with ethylene oxide; block polymers of ethylene oxide and propylene oxide; or alkyldimethylamine oxides.

The surfactants can also be anionic compounds, such as soaps; fatty sulfate esters, for example dodecyl sodium sulfate, octadecyl sodium sulfate and cetyl sodium sulfate; alkylsulfonates, arylsulfonates and fatty-aromatic sulfonates, such as alkylbenzenesulfonates, for example calcium dodecylbenzenesulfonate, and butylnaphthalenesulfonates; and more complex fatty sulfonates, for example the amide condensation products of oleic acid and N-methyltaurine and sodium dioctyl sulfosuccinate.

Finally, the surfactants can be cationic compounds, such as alkyldimethylbenzylammonium chlorides, dialkyldimethylammonium chlorides, alkyltrimethylammonium chlorides and ethoxylated quaternary ammonium chlorides.

Suitable dispersants (without surfactant action) are mainly: sodium salts and ammonium salts of lignosulfonic acid, sodium salts of maleic anhydride/diisobutylene copolymers, sodium salts and ammonium salts of sulfonated polycondensation products of naphthalene with formaldehyde, sodium salts of polymeric carboxylic acids and sulfite waste liquors.

Examples of dispersants which can be used and are suitable in particular as thickeners or antisettling agents are methylcellulose, carboxymethylcellulose, hydroxyethylcellulose, polyvinyl alcohol, alginates, caseinates and blood albumin.

Examples of suitable stabilisers are acid-binding agents, for example epichlorohydrin, phenyl glycidyl ether and soya epoxides; antioxidants, for example gallic esters and butylhydroxytoluene; UV absorbers, for example substituted benzophenones, α-cyano-β,β-diphenylacrylic esters and cinnamic esters; and deactivators, for example salts of ethylenediaminetetraacetic acid and polyglycols.

Apart from the combinations according to the invention, the fungicidal compositions according to the invention can also contain other active substances, for example other fungicidal compositions [active substance components c) or d)]; insecticides and acaricides, bactericides, plant-growth regulators and fertilisers. These combination agents are suitable for widening the activity spectrum or for other favourable effects on the plant growth.

Depending on their type, the fungicides according to the invention in general contain between 0.0001 and 95 percent by weight of the active substance combination according to the invention. In concentrates, the active substance concentration is usually in the upper region of the upper concentration interval. These forms can then be diluted with identical or different formulation agents to give active substance concentrations suitable for practical use, and these concentrations are usually in the lower region of the upper concentration interval. Emulsifiable concentrates in general contain 5 to 95 percent by weight, preferably 25 to 85 percent by weight, of the active substance combination according to the invention. Suitable application forms are, inter alia, ready-to-use solutions, emulsions and suspensions which are suitable, for example, as spray mixtures. In spray mixtures of this type, for example, concentrations between 0.0001 and 20 percent by weight can be present. In the ultralow volume process, it is possible to formulate spray mixtures in which the active substance concentration is preferably 0.5 to 20 percent by weight, while the spray mixtures formulated in the low-volume process and the high-volume process preferably have an active substance concentration of 0.02 to 1.0 or 0.002 to 0.1 percent by weight.

The fungicidal compositions according to the invention can be prepared by mixing an active ingredient combination according to the invention with formulation agents.

The compositions can be prepared in a known manner, for example by intimate mixing of the active substances with solid carriers, by dissolution or suspension in suitable solvents or dispersants, if appropriate with the use of surfactants as wetting agents or emulsifiers or of dispersants, by dilution of already prepared emulsifiable concentrates using solvents and dispersants, and the like.

In the case of pulverulent compositions, the active substances can be mixed with a solid carder, for example by joint grinding; or the solid carrier can be impregnated with a solution or suspension of the active substances and the solvent or dispersant can then be removed by slow evaporation, heating or by suction under reduced pressure. By adding surfactants or dispersants, pulverulent compositions of this type can be made easily water-wettable, enabling them to be convened into aqueous suspensions, which are suitable, for example, as sprays.

The active substance mixtures according to the invention can also be mixed with a surfactant and a solid carrier in order to form a wettable powder, which is dispersible in water, or they can be mixed with a solid pregranulated carder in order to form a granulated product.

If desired, the active substance mixtures according to the invention can be dissolved in a water-immiscible solvent, for example an alicyclic ketone, which advantageously contains a dissolved emulsifier, so that the solution has a self-emulsifying effect when added to water. Otherwise, the active substance combinations can be mixed with an emulsifier and the mixture can be then diluted with water to the desired concentration. Moreover, the active substance combinations can be dissolved in a solvent and then mixed with an emulsifier. Such a mixture can likewise be diluted with water to the desired concentration. This gives emulsifiable concentrates or ready-to-use emulsions.

The compositions according to the invention can be used by the application methods customary in plant protection or agriculture. The process according to the invention for controlling harmful fungi comprises treating the location of plant growth to be protected or the plant material to be protected, for example plants, parts of plants or plant propagation material (e.g. seed), with an active amount of an active substance combination according to the invention or a composition according to the invention.

FORMULATION EXAMPLES

EXAMPLE 1: Emulsifiable Concentrate (EC)

| | |
|---|---|
| Fenpropimorph | 300 g/L |
| Cyproconazol | 50 g/L |
| N-Methylpyrrolidone (solvent aid) | 100 g/L |
| Nonylphenol polyethoxylate (nonionic emulsifier) | 50 g/L |
| Calcium dodecylbenzenesulfonate (anionic emulsifier) | 25 g/L |
| Alkylbenzene mixture (solvent) balance | to 1000 ml |

Such a concentrate can be diluted with water to give application mixtures for the treatment of leaves, the treatment of soil or the treatment of parts of plants.

EXAMPLE 2: Emulsifiable Concentrate (EC)

| | |
|---|---|
| Fenpropimorph | 120 g/L |
| Fenpropidin | 240 g/L |
| Cyproconazol | 50 g/L |
| N-Methylpyrrrolidone (solvent aid) | 100 g/L |
| Isotridecanol polyethoxylate (nonionic emulsifier) | 75 g/L |
| Calcium dodecylbenzenesulfonate (anionic emulsifier) | 25 g/L |
| Alkylnaphthalene mixture (solvent) balance | to 1000 ml |

All components are dissolved with stirring, the dissolution process being accelerated by gentle heating. In dilute form, solutions of this type are used for protecting plants or parts of plants (seeds, cuttings, tubers, and the like) against infestation with fungi.

EXAMPLE 3: Emulsifiable Concentrate (EC)

| | |
|---|---|
| Fenpropimorph | 50 g/L |
| Fenpropidin | 50 g/L |
| Cyproconazol | 25 g/L |
| Octylphenol polyethylene glycol ether (4–5 mol of ethylene oxide) | 30 g/L |
| Calcium dodecylbenzenesulfonate | 30 g/L |
| Castor oil polyglycol ether (35 mol of ethylene oxide) | 40 g/L |
| Cyclohexanone | 300 g/L |
| Xylene mixture | to 1000 ml |

The resulting solutions are emulsified in water according to Example 1–3 and thus produce a ready-to-use spray mixture in a desired dilution. A spray mixture of this type can be used to dress, for example, cereal seeds.

EXAMPLE 4: Wettable powder (WP)

| | |
|---|---|
| Fenpropidin | 25% w/w |
| Cyproconazol | 25% w/w |
| Hydrated silica (silica carrier) | 25% w/w |
| Nonylphenol polyethoxylate (wetting agent) | 4% w/w |
| Sodium polycarboxylate (dispersant) | 4% w/w |
| Calcium carbonate (inert material, carrier) | 17% w/w |

To prepare this wettable powder, fenpropidin and nonylphenol polyethoxylate are mixed in a first working procedure and sprayed onto the initially introduced silica in a powder mixer.

The further components are then admixed and milled, for example, in a pinned disc mill to a fine powder.

The resulting wettable powder, when stirred into water, gives a fine suspension in the desired dilution, which is suitable as ready-to-use spray mixture, for example for dressing plant propagation material, such as plant tubers, root material and leaf material of seedlings or of plant seeds.

EXAMPLE 5: Wettable Powder (WP)

| | |
|---|---|
| Fenpropimorph | 15% w/w |
| Fenpropidin | 25% w/w |
| Cyproconazol | 10% w/w |
| Sodium lignosulfonate | 5% w/w |
| Sodium diisobutylnaphthalenesulfonate | 6% w/w |
| Octylphenol polyethylene glycol ether (7–8 mol of ethylene oxide) | 2% w/w |
| Highly disperse silica | 10% w/w |
| Kaolin | 27% w/w |

EXAMPLE 6: Wettable Powder (WP)

| | |
|---|---|
| Fenpropimorph | 50% w/w |
| Fenpropidin | 20% w/w |
| Cyproconazol | 5% w/w |
| Sodium lauryl sulfate | 5% w/w |
| Sodium diisobutylnaphthalenesulfonate | 10% w/w |
| Highly disperse silica | 10% w/w |

The active ingredients from Examples 5 and 6 are thoroughly mixed with the additives and thoroughly ground in a suitable mill. This gives wettable powders which can be diluted with water to give suspensions of any desired dilution.

EXAMPLE 7: Dusts

| | |
|---|---|
| Fenpropimorph | 6% w/w |
| Cyproconazol | 2% w/w |
| Kaolin | 87% w/w |
| Highly disperse silica | 5% w/w |

Dusts ready for application are obtained by mixing the active substances with the carrier and grinding the mixture in a suitable mill.

Biological Examples

B-1. Mycelium growth test using *Helminthosporium repentis-tritici* a) Method:

The fungal strain is cultured at 18° C. and 16 hours/day of simulated sunlight irradiation for 7 days on potato-dextrose-agar (PDA), which contains one of the two or both active substances or is free of active substance (control). To this end, active substances I and II are each dissolved in pure ethanol and mixed in the desired relative amounts and diluted. A specified amount is then added to the liquid PDA medium at 50° C. and intimately mixed therewith. Agar media having active substance concentrations of 30; 10; 3; 1; 0.3; 0.1; 0.03 and 0.01 mg of a.i./litre are prepared. The ethanol concentration in the medium is uniformly 0.1%.

The liquid culture medium is then poured into Petri dishes (9 cm diameter) and inoculated in the centre using an agar disc (5 mm diameter), which was stamped out from a 7 day old fungal culture. The inoculated dishes are incubated at 18° C. in an air-conditioned chamber in the dark for 5 days. Each test is repeated 3 or 4 times.

b) Evaluation:

After the incubation period, the diameter of the colony is determined. The fungicidal actions according to Abbott are convened into small probit values (Bliss, C. I. 1935)[*] plotted against the logarithms of the fungicide concentrations to give a dose-action relationship. This probit-log graph converts the dose/action curve into a straight line (D. L. Finney 1971 "Probit analysis", 3rd edition, Cambridge, UK: Cambridge University Press). The linear regression and the ED-50 values (effective dosage) are determined from this straight line.

[*] Bliss, C. I. Ann. Appl. Biol. 22, 134–167 (1935)

Calculation of the synergistic factors (SF) of fungicides in a mixture

The theoretical effect ($ED_{th}$) of a mixture can be calculated using the formula of Wadley (**) if the ED values of the individual components of the mixture are known:

[**] Wadley, F. M. (1945) The evidence required to show synergistic action of insecticides and a short cut in analysis. ET-223, U.S. Department of Agriculture, 8 pp. Wadley, F. M. (1967) Experimental Statistics in Entomology. Washington, U.S.A.: Graduate School Press, U.S.D.A.

$$ED\text{-}50\ (th) = \frac{a+b}{\frac{a}{ED\text{-}50_a} + \frac{b}{ED\text{-}50_b}}$$

a,b = ratios of the fungicides in the mixture.

The ratio of the calculated theoretical effect ($ED_{th}$) and the actually observed effect ($ED_{ob}$) of the mixture gives the synergic factor (SF).

$$SF = \frac{ED\text{-}50\ (th)}{ED\text{-}50\ (ob)}$$

| | |
|---|---|
| $SF > 1.2$ | synergistic interaction |
| $SF > 0.5 < 1.2$ | additive interaction |
| $SF < 0.5$ | antagonistic interaction |

According to U. Gisi et al. (1987) and Y. Levy et al. (1986), a synergistic interaction is already observed with SF values of greater than 1.0.[***]

[***] Gisi, U., Binder, H., Rimbach, E. (1985) Synergistic interactions of fungicides with different modes of action. Trans. Br. mycol. Soc. 85 (2), 299–306 Levy, Y. et al. (1986) The joint action of fungicides in mixture: comparison of two methods of synergy calculation Bulletin OEPP 16, 651–657 (1986)

The limits of the synergistic factor of a certain mixture are determined using the standard deviation of the ED values observed. SF values of greater than 1.2 give a statistically significant synergism.

d) Test results using active substance I and active substance II

Activities of the individual components and of the mixture (ED-50)

TABLE 1

| Active substance | Test No. | | | |
|---|---|---|---|---|
| | 1 | 2 | 3 | 4 |
| I | 9.0 | 30.9* | 13.1 | 12.9 |
| II | 2.5 | 1.9 | 1.9 | 0.8 |
| I:II = 1:1 | 1.8 | 1.9 | 2.3 | 0.8 |
| SF of the ED-50 values | 2.2 | 1.9 | 1.4 | 1.9 |

* = calculated value (outside the measuring range)

e) Test results using active substance I and active substance III

Activities of the individual components and of the mixture (ED-50)

TABLE 2

| Active substance | Test No. | | | |
|---|---|---|---|---|
| | 1 | 2 | 3 | 4 |
| I | 9.0 | 30.9* | 13.1 | 12.9 |
| III | 3.6 | 3.2 | 2.8 | 0.8 |
| I:III = 1:1 | 1.9 | 2.3 | 1.6 | 0.6 |
| SF of the | 2.7 | 2.5 | 2.9 | 2.5 |

TABLE 2-continued

| Active substance | Test No. 1 | 2 | 3 | 4 |
|---|---|---|---|---|
| ED-50 values | | | | |

* = calculated value (outside the measuring range)

B-2. Mycelium growth test using *Septoria nodorum*

The test method and its evaluation are similar to that of Biological Example B-1.

a) Test results using active substance I and active substance II

Activities of the individual components and of the mixture (ED-50)

TABLE 3

| Active substance | Test No. 1 | 2 |
|---|---|---|
| I | 0.7 | 0.3 |
| II | 0.8 | 0.4 |
| I:II = 1:1 | 0.4 | 0.1 |
| SF of the ED-50 values | 1.9 | 3.4 | b) Test results using active substance I and active substance III

Activities of the individual components and of the mixtures (ED-50)

TABLE 4

| Active substance | Test No. 1 | 2 |
|---|---|---|
| I | 0.7 | 0.3 |
| III | 1.4 | 1.3 |
| I:III = 1:1 | 0.7 | 0.3 |

TABLE 4-continued

| Active substance | Test No. 1 | 2 |
|---|---|---|
| SF of the ED-50 values | 1.3 | 1.6 | f) Comment

The values from Tables 1 to 4 show for each of the independently run tests that the fungicidal action of a mixture comprising active substance I and active substance II and of a mixture comprising active substance I and active substance III undergoes a significant increase, i.e. a synergistically increased action is present. As can be seen, these actions are each time reproducible.

Similar results are also obtained with Helminthosporium teres.

What is claimed is:

1. A fungicidal composition containing at least two active ingredients:

a) cyproconazol or an acid addition salt or metal complex thereof and b) fenpropimorph or an acid addition salt thereof and a carrier, wherein the weight ratio of active ingredients a): b) is in the range of 1:1 to 1:10.

2. A process for controlling fungi, which comprises the step of treating a location infected or liable to be infected with fungi with a fungicidally-effective amount of a combination of cyproconazol and fenpropimorph in a weight ratio in the range of 1:1 to 1:10.

3. The process of claim 2, wherein the location is treated with cyproconazol and fenpropimorph simultaneously.

4. The process of claim 2, wherein the location treated is plant propagation material.

5. The process of claim 4, wherein the plant propagation material is a seed.

* * * * *